(12) United States Patent
Dasgupta et al.

(10) Patent No.: US 10,534,083 B2
(45) Date of Patent: Jan. 14, 2020

(54) SYSTEM AND METHOD FOR ULTRASOUND COLOR DOPPLER IMAGING

(71) Applicant: TEXAS INSTRUMENTS INCORPORATED, Dallas, TX (US)

(72) Inventors: Udayan Dasgupta, Karnataka (IN); David P. Magee, Allen, TX (US); Murtaza Ali, Cedar Park, TX (US)

(73) Assignee: TEXAS INSTRUMENTS INCORPORATED, Dallas, TX (US)

( * ) Notice: Subject to any disclaimer, the term of this patent is extended or adjusted under 35 U.S.C. 154(b) by 197 days.

(21) Appl. No.: 15/458,054

(22) Filed: Mar. 14, 2017

(65) Prior Publication Data

US 2017/0184720 A1 Jun. 29, 2017

Related U.S. Application Data

(62) Division of application No. 12/490,709, filed on Jun. 24, 2009, now abandoned.

(Continued)

(51) Int. Cl.
*G01S 15/89* (2006.01)
*A61B 8/06* (2006.01)
(Continued)

(52) U.S. Cl.
CPC ............ *G01S 15/8981* (2013.01); *A61B 8/06* (2013.01); *A61B 8/461* (2013.01); *A61B 8/488* (2013.01);
(Continued)

(58) Field of Classification Search
CPC ....... A61B 8/06; A61B 8/488; G06F 9/30098; G06F 9/30145
See application file for complete search history.

(56) References Cited

U.S. PATENT DOCUMENTS 4,719,923 A 1/1988 Hartwell et al.
4,809,703 A 3/1989 Ishikawa et al.
(Continued)

OTHER PUBLICATIONS

Bjaerum, Steinar et al., "Clutter Filter Design for Ultrasound Color Flow Imaging," IEEE Transactions on Ultrasonics, Ferroelectrics, and Frequency Control, vol. 49, No. 2, Feb. 2002, pp. 204-216.
(Continued)

*Primary Examiner* — Tse W Chen
*Assistant Examiner* — Jason M Ip
(74) *Attorney, Agent, or Firm* — John R. Pessetto; Charles A. Brill; Frank D. Cimino (57) ABSTRACT

Systems and methods for color Doppler imaging in an ultrasound imaging system are disclosed herein. An ultrasound imaging system includes color Doppler imaging circuitry. The color Doppler imaging circuitry is configured to estimate flow parameters. The imaging circuitry includes a radio frequency ("RF") demodulator configured to produce in-phase and quadrature components of an ultra-sound data vector. The RF demodulator includes a table in memory that stores interleaved sine and cosine values. The RF demodulator maintains an index value for the table having higher precision than is used to index the table. The RF demodulator rounds the index value for each access of the table. Each table access retrieves a sine value and a cosine value.

2 Claims, 7 Drawing Sheets

Related U.S. Application Data (60) Provisional application No. 61/143,676, filed on Jan. 9, 2009, provisional application No. 61/087,019, filed on Aug. 7, 2008, provisional application No. 61/077,917, filed on Jul. 3, 2008.

(51) Int. Cl.
*A61B 8/08* (2006.01)
*A61B 8/00* (2006.01)
*G01S 7/52* (2006.01)

(52) U.S. Cl.
CPC ........ *A61B 8/5207* (2013.01); *G01S 7/52095* (2013.01)

(56) References Cited

U.S. PATENT DOCUMENTS

| | | |
|---|---|---|
| 5,058,594 A | 10/1991 | Lazenby |
| 5,349,524 A * | 9/1994 | Daft .................. G01S 7/52071 367/135 |
| 5,349,525 A | 9/1994 | Dunki-Jacobs et al. |
| 5,488,588 A | 1/1996 | Engeler et al. |
| 5,555,534 A | 9/1996 | Maslak et al. |
| 5,823,964 A | 10/1998 | Liu et al. |
| 6,032,170 A | 2/2000 | Guttag et al. |
| 6,135,961 A | 10/2000 | Pflugrath et al. |
| 6,151,705 A | 11/2000 | Santhanam |
| 6,648,826 B2 | 11/2003 | Little et al. |
| 6,924,823 B2 | 8/2005 | Maruyama et al. |
| 7,604,596 B2 | 10/2009 | Hwang et al. |
| 2002/0091319 A1 | 7/2002 | Moehring et al. |
| 2002/0144084 A1 | 10/2002 | Takayama et al. |
| 2003/0097391 A1 * | 5/2003 | Saulsbury ............. G06F 7/5443 708/490 |
| 2003/0120905 A1 | 6/2003 | Stotzer et al. |
| 2003/0163047 A1 | 8/2003 | Little et al. |
| 2004/0003386 A1 | 1/2004 | Tal et al. |
| 2004/0015934 A1 | 1/2004 | Muthukumar et al. |
| 2004/0133110 A1 | 7/2004 | Little et al. |
| 2005/0265267 A1 | 12/2005 | Hwang |
| 2008/0126460 A1 | 5/2008 | Jiang et al. |
| 2008/0180578 A1 | 7/2008 | Jaffe |
| 2008/0267513 A1 | 10/2008 | Sankaran |
| 2009/0227868 A1 | 9/2009 | Dong |
| 2010/0012119 A1 | 1/2010 | Sallak et al. |

OTHER PUBLICATIONS

Kasai, Chihiro et al., "Real-Time Two Dimensional Blood Flow Imaging Using an Autocorrelation Technique," IEEE Transaction on Sanies and Ultrasonics, vol. SU-32, No. 3, May 1985, pp. 458-464.

Loupas, Thanasis et al., "Experimental Evaluation of Velocity and Power Estimation for Ultrasound Blood Flow Imaging, by Means of a Two-Dimensional Autocorrelation Approach," IEEE Transactions on Ultrasonics, D Ferroelectrics, and Frequency Control, vol. 42, No. 4, Jul. 1995, pp. 689-699.

Zheng, Yi et al., "Stable and Unbiased Flow Turbulence Estimation from Pulse Echo Ultrasound," IEEE Transactions on Ultrasonics, Ferroelectrics, and Frequency Control, vol. 46, No. 5, Sep. 1999, pp. 1074-1087.

* cited by examiner

SYSTEM AND METHOD FOR ULTRASOUND COLOR DOPPLER IMAGING

The present application is a divisional of U.S. patent application Ser. No. 12/490,709 which claims priority to and incorporates by reference provisional patent application 61/077,917, filed on Jul. 3, 2008, entitled "Efficient Implementation of Ultrasound Color Doppler Algorithms Using Partial Sums," provisional patent application 61/087,019, filed on Aug. 7, 2008, entitled "Efficient Implementation of Ultrasound Color Doppler Algorithms," and provisional patent application 61/143,676, filed on Jan. 9, 2009, entitled "Efficient Implementation of Ultrasound Color Doppler Algorithms on VLIW Architectures."

BACKGROUND

Ultrasound systems are becoming increasingly important tools for non-invasive medical diagnostics. Consequently, ultrasound imaging systems featuring reduced power consumption and improved portability are desirable. Digital signal processors ("DSPs") have been used to reduce power and increase portability of various types of medical imaging systems, including ultrasound systems.

The most common operating modes of ultrasound systems are Brightness mode ("B-mode") and Color Doppler Mode. In B-mode, an ultrasound system transmits sound waves of a particular frequency into the body of interest and records the received echoes as a function of time and position to image structural information. The brightness of each point on a display represents the amplitude of the sampled echoes. Color Doppler mode is similar to B-mode but transmits multiple pulses (an ensemble) and uses the relative time (phase) between received echoes to estimate blood flow characteristics. Commonly estimated flow parameters include flow strength (power), direction, velocity, and turbulence.

SUMMARY

A system and method for color Doppler imaging in an ultra-sound system are disclosed herein. In one embodiment, an ultrasound imaging system includes color Doppler imaging circuitry. The color Doppler imaging circuitry is configured to estimate flow parameters. The imaging circuitry includes a radio frequency ("RF") demodulator configured to produce in-phase and quadrature components of an ultrasound data vector. The radio frequency demodulator includes a table in memory that stores interleaved sine and cosine values. The radio frequency demodulator maintains an index value for the table having higher precision than is used to index the table. The radio frequency demodulator rounds the index value for each access of the table. Each table access retrieves a sine value and a cosine value.

In another embodiment, a method includes fetching from ultrasound imaging system memory, in a single memory access cycle, a plurality of Wall filter coefficients. The plurality of Wall filter coefficients are applied to a plurality of complex ultrasound data values in a single execution cycle. Wall filtered ultrasound data is provided to a flow estimator.

In another embodiment, an ultrasound color Doppler imaging system includes a processor and a software system for color Doppler imaging executed by the processor. The software system includes instructions that when executed cause the processor to convert real radio frequency ("RF") ultrasound samples to complex RF ultrasound samples using sine and cosine values stored in adjacent memory locations.

In yet another embodiment, a color Doppler imaging system includes circuitry that computes a sum of powers of a first ensemble and a sum of powers of a second ensemble. The system also includes circuitry that stores the sum of powers of the first ensemble and the sum of powers of the second ensemble in memory. The system further includes circuitry that retrieves the sum of powers of the first ensemble and the sum of powers of the second ensemble from memory and computes a flow power parameter using the retrieved sums of powers.

BRIEF DESCRIPTION OF THE DRAWINGS

For a detailed description of exemplary embodiments of the invention, reference will now be made to the accompanying drawings in which.

NOTATION AND NOMENCLATURE

Certain terms are used throughout the following description and claims to refer to particular system components. As one skilled in the art will appreciate, companies may refer to a component by different names. This document does not intend to distinguish between components that differ in name but not function. In the following discussion and in the claims, the terms "including" and "comprising" are used in an open-ended fashion, and thus should be interpreted to mean "including, but not limited to . . . ." Also, the term "couple" or "couples" is intended to mean either an indirect or direct electrical connection. Thus, if a first device couples to a second device, that connection may be through a direct electrical connection, or through an indirect electrical connection via other devices and connections. Further, the term "software" includes any executable code capable of running on a processor, regardless of the media used to store the software. Thus, code stored in memory (e.g., non-volatile memory), and sometimes referred to as "embedded firmware," is included within the definition of software. The terms "ultrasound" or "ultrasonic" generally refer to acoustic waves at frequencies beyond the range of human hearing (e.g., frequencies above 20 KHz).

DETAILED DESCRIPTION

The following discussion is directed to various embodiments of the invention. Although one or more of these embodiments may be preferred, the embodiments disclosed should not be interpreted, or otherwise used, as limiting the scope of the disclosure, including the claims. In addition, one skilled in the art will understand that the following description has broad application, and the discussion of any embodiment is meant only to be exemplary of that embodiment, and not intended to intimate that the scope of the disclosure, including the claims, is limited to that embodiment.

Color Doppler mode ultrasound involves estimating blood flow characteristics using Doppler techniques, and is employed to diagnose a variety of conditions, for example blood clots, valve defects and blocked arteries. The processing demands make color Doppler mode one of the more computationally intensive applications of ultrasound. The high computational demands of color Doppler mode have required hardware implementations. Unfortunately, hardware implementations can be restrictive and expensive. Embodiments of the present disclosure exploit novel processing algorithms that allow implementation of color Doppler mode ultra-sound in hardware or via software executed on a processor, for example, a very long instruction word ("VLIW") processor, such as a C64X+™ processor produced by Texas Instruments Incorporated.

Figure 1:
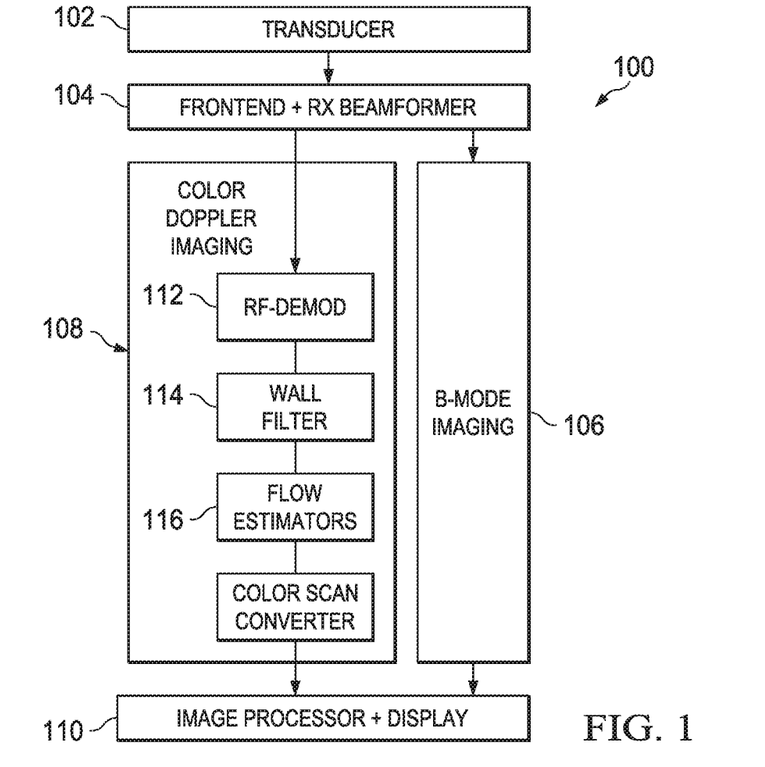
FIG. 1 shows a block diagram of a receiver path of an ultra-sound imaging system configured to perform color Doppler imaging in accordance with various embodiments.

FIG. 1 shows a block diagram of a receive path 100 of an ultra-sound imaging system configured to perform color Doppler imaging in accordance with various embodiments. Ultrasound receivers use amplitude and phase information from reflected sound waves to provide structural and functional information about a body of interest. The receive path 100 includes a transducer 102, receiver frontend/beamformer circuitry 104, a brightness mode ("B-mode") imaging system 106, a color Doppler mode imaging system 108, and an image processor/display 110. The transducer 102 detects ultrasonic waves reflected by internal structures of the subject and converts the detected sound waves (i.e., pressure waves) into electrical signals. The transducer 102 can comprise a piezoelectric crystal, electro-magnetic transducer, micro-electro-mechanical system ("MEMS") transducer or other device that converts sound waves into an electrical signal. Moreover, the transducer 102 can comprise one or more transducer elements. In some embodiments, the transducer 102 can convert electrical drive signals generated by a transmitter into sound waves that are introduced into the subject to be imaged, for example, a human body when considering medical ultrasound. In some embodiments, the same transducer elements are used to generate ultrasonic waves and to detect ultrasonic waves. In other embodiments, separate transducer elements are used for wave generation and detection.

The receiver frontend/beamformer 104 receives the sound signals detected by the transducer 102. The receiver frontend/beamformer 104 amplifies, filters, and digitizes the received signals. The digitized signals are scaled and delayed to permit coherent summation. The beamformed signal is provided to the B-mode imaging system 106 and/or the color Doppler mode imaging system 108.

The color Doppler mode imaging system 108 includes a radio frequency ("RF") demodulator 112, a Wall filter 114, and flow estimators 116. The RF demodulator 112 mixes, filters, and decimates echo data. RF demodulation is used for B-mode as well as color Doppler mode processing. In color Doppler mode, the input to the RF demodulator 112 is multiple ensembles of scan lines. There may be, for example, B scan line sets where each set consists of N scan lines. Thus, the ensemble size is N. Each scan line consists of T real valued RF data samples. The RF demodulator 112 produces decimated in-phase (I) and quadrature (Q) components for each of the scan lines, where the decimation factor is S and the decimation filter includes L taps. Thus, the RF demodulator produces an output scan line including D (equal to T/S) decimated points. The Wall filter uses D sets (ensembles) of scan lines, each set consisting of N decimated points, to generate D flow or power estimates. The purpose of the Wall filter 114 is to process the demodulated echo data and filter out the motion of blood vessel walls. The flow estimators 116 can include a color flow estimator and/or a flow power estimator. The color flow estimator estimates blood flow velocity, turbulence and power. The flow power estimator estimates only the flow power and is used to determine the strength of blood flow or the presence of blood.

Embodiments of the present disclosure employ an RF demodulator, Wall Filter, and/or flow estimators using novel processing methods that improve the performance of the color Doppler imaging system 108. More specifically, embodiments improve the performance of the color Doppler imaging system 108 when implemented on a processor, such as a VLIW processor.

In at least some embodiments of the ultra-sound imaging system receive path 100, at least some of the operations discussed herein, for example, the RF demodulator 112, the Wall filter 114, and/or the flow estimators 116 algorithmic operations described below can be implemented via software programming executed by a processor, such as a DSP or VLIW processor. Software programming can be stored in a computer readable medium, such as a semiconductor memory device, a magnetic or optical storage device, etc. accessible to the processor. In some embodiments, at least some of the operations of the RF demodulator 112, the Wall filter 114, and/or the flow estimators 116 may be implemented in dedicated hardware circuitry, for example an application specific integrated circuit ("ASIC") or field programmable gate array ("FPGA").

When attempting to optimize an algorithm for any architecture, it is useful to create complexity targets for the exercise. Towards this end, a simple "best-case" complexity analysis is presented to establish a lower bound for the complexity (DSP cycles) of the subject algorithms on the Texas Instruments' C64x+™ core. Although embodiments are explained with respect to C64x+ cores, the general methodology presented is applicable to other VLIW architectures.

Figure 2:
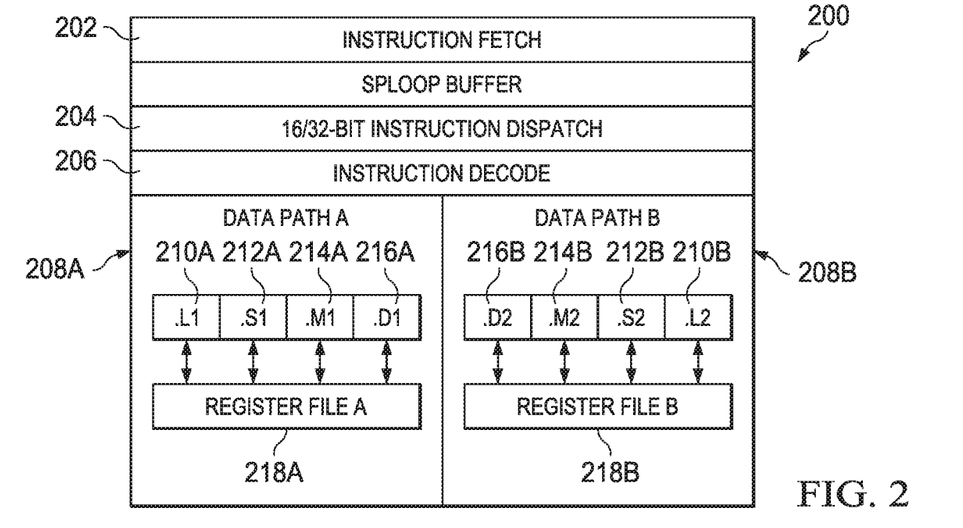
FIG. 2 shows a very long instruction word ("VLIW") processor architecture for implementing color Doppler imaging in accordance with various embodiments.

FIG. 2 shows a VLIW processor architecture (a TI C64x+ architecture) 200 for implementing color Doppler imaging. Various elements of the VLIW processor architecture 200 such as control logic, cache memories, clock circuitry, interrupt circuitry, peripherals, interconnecting buses, processor input/output ports, etc. have been omitted for clarity. During every clock cycle in the TI C64x+ platform, the instruction fetch 202, dispatch 204, and decode units 206 deliver instructions to the eight functional units that reside in two data paths (A 208A and B 208B). Each data path contains four functional units (L 210A/B, S 212A/B, M 214A/B, and D 216A/B) and a register file 218A/B including 32 general-purpose 32-bit registers. Generally, the L units 210A/B are configured for 32/40-bit arithmetic operations and 32-bit logical operations, the S units 212A/B are configured for 32-bit arithmetic and logic operations and 40-bit shifting, the M units 214A/B are configured to perform multiplication, and the D units 216A/B are configured for various data load/store operations and 32-bit addition/subtraction and address computation. Unless otherwise noted, every unit (L 210A/B, S 212A/B, M 214 A/B, and D 216 A/B) produces a result at each clock cycle when the operations are pipelined perfectly. TI C64X+ instructions referred to herein include:

ADD—add two signed integers without saturation.
DPACK2—parallel PACK2 and PACKH2 operations.
DOTP2—dot product of two pairs of signed, packed 16-bit values.
DOTPN2—dot product of two pairs of signed, packed 16-bit values where the second product is negated.
LDW—load word (32-bits) from memory.
LDDW—load double word (64-bits) from memory.
MPY2IR—perform two 16-bit by 32-bit multiplies, including a round and a shift by 15 bits to produce 32-bit results.
PACK2—move the lower half-word (16-bits) of src1 into the upper half-word of dest, and the lower half-word of src2 into the lower half-word of dest.
PACKH2—move the upper half-word of src1 into the upper half-word of dest and the upper half-word of src2 into the lower half-word of dest.
PACKLH2—move the lower half-word of src1 into the upper half-word of dest and the upper half-word of src2 into the lower half-word of dest.
SADD—add two signed integers, saturate the result.
SPACK2—saturate two 32-bit values to signed 16-bit values and pack them into upper and lower register halves.
STDW—store double word (64-bits) to memory.

The complexity of the each algorithm is approximated by the complexity of the loop kernels, which dominate complexity of these algorithms. The complexity analysis is "best-case" in the sense that it does not attempt to estimate overheads and is a first order approximation of the complexity. Overheads include epilog and prolog of loop kernels, outer loop operations in nested-loop implementations, etc. In order to achieve these estimates, an implementation may need to change the algorithm data path (without affecting performance) to get the lowest complexity on the C64x+™ core. To arrive at these estimates, the most efficient data flow and CPU instructions are estimated for each of the algorithmic operations. Then the various functional units to which these instructions can be mapped are considered and the cycles on the unit that is most loaded is used as the estimate of the algorithm's complexity. Note that perfect pipelining performance is assumed.

Throughout this disclosure lower-case letters are used as indexes into quantities whose maximum values are indicated by their upper-case counterparts, e.g. t is an index into the T RF points of each scan line. Also upper case letters denote matrices and vectors while their lower case counterparts denote the individual elements in these matrices/vectors, e.g. r is an element of vector R. The subscripts used with matrices denote their dimensions whereas subscripts used with elements denote their positions in the matrix/vector, e.g. $r_t$ denotes the $t^{th}$ element in the vector R, whereas $R_T$ denotes that R is a vector of length T.

In some embodiments of the color Doppler imaging system 108, the RF demodulator 112 takes 32-bit inputs and produces 16-bit decimated results. In such embodiments, the input and output bit precision for other modules (e.g., Wall filter 114) may be 16-bit, with the exception of the flow estimates produced by the flow estimators 116, which may be 8-bits each. All tables and filter coefficients may be 16-bit, unless otherwise stated. Software embodiments may be implemented using the C programming language and compiler intrinsics (e.g., special functions that map to inlined processor instructions), and without use of assembly language. Embodiments have been implemented using normalized mean square error and normalized maximum absolute error targets of 1e-6 and 1e-3. The normalization of the metrics was with respect to floating point outputs.

Returning now to the RF Demodulator 112, for a given transducer center frequency $f_c$, and front end sampling frequency $f_s$, the RF demodulator 112 mixes the beamformed RF data received from the frontend 104 for each scan line, $R_T$, to create in-phase and quadrature components of the vector, $M_T$.

$$\text{Re}\{m_t\} = r_t \cdot \cos(kt), k = \frac{2\pi f_c}{f_s}, 0 \le t < T-1, \quad (1a)$$

$$\text{Im}\{m_t\} = r_t \cdot \sin(kt), k = \frac{2\pi f_c}{f_s}, 0 \le t < T-1. \quad (1b)$$

These mixed outputs, $M_T$, are then passed through a low-pass filter, F, to prevent aliasing and down-sampled in a single step, to generate the decimated output vector, $E_D$.

$$\text{Re}\{e_d\} = \sum_{l=0}^{L} f_l \cdot \text{Re}\{m_{t-l}\}, 0 \le d \le D-1, t = Sd, \quad (2a)$$

$$\text{Im}\{e_d\} = \sum_{l=0}^{L} f_l \cdot \text{Im}\{m_{t-l}\}, 0 \le d \le D-1, t = Sd. \quad (2b)$$

As shown in equations (1a-1b), the mixing operation involves multiplication of an RF value $r_t$ by a sine value and a cosine value. The sine and cosine values needed for the mixing operation can be stored in tables or computed on the fly. From a complexity perspective, tables are preferable provided they can be kept reasonably small. One approach is using a table corresponding to sin(2πkt) and cos(2πkt) for all possible t. Although this approach provides high precision and easy linear indexing, the tables may be large (T 16-bit values) and would need to be regenerated for every change of k, resulting from a change of scanning parameters.

Embodiments of the present disclosure include a small table (for example, a 2 kilo-byte table consisting of 512 sine and 512 cosine values with each value represented by a 16-bit number, is sufficient in some embodiments) containing a cycle of interleaved sine and cosine data (sin(2πt)/cos(2πt)) and index the table circularly using k. Embodiments provide adequate performance using the small table by maintaining a total indexing value at a high precision (e.g., a 32-bit number) and rounding the indexing value to the closest table index only for look-up purposes. Thus, all table index increments use 32-bits although indexing of the table would use fewer bits (e.g., 9 bits). Using such a table is advantageous because a single table suffices for a variety of parameter settings—with only the step-size for table indexing, k, changed for different parameter settings. Although it is possible to generate the cosine values from the sine table by appropriate offsets, a larger table with interlaced 16-bit sine/cosine values is preferable to simplify indexing and to allow access to both sine and cosine values for a point using a single 32-bit load. To simplify indexing, a complete cycle of the sinusoid is preferably stored, rather than storing a quarter sinusoid and using more complex indexing. To further simplify table indexing, the table length is preferably a power of two.

Figure 3:
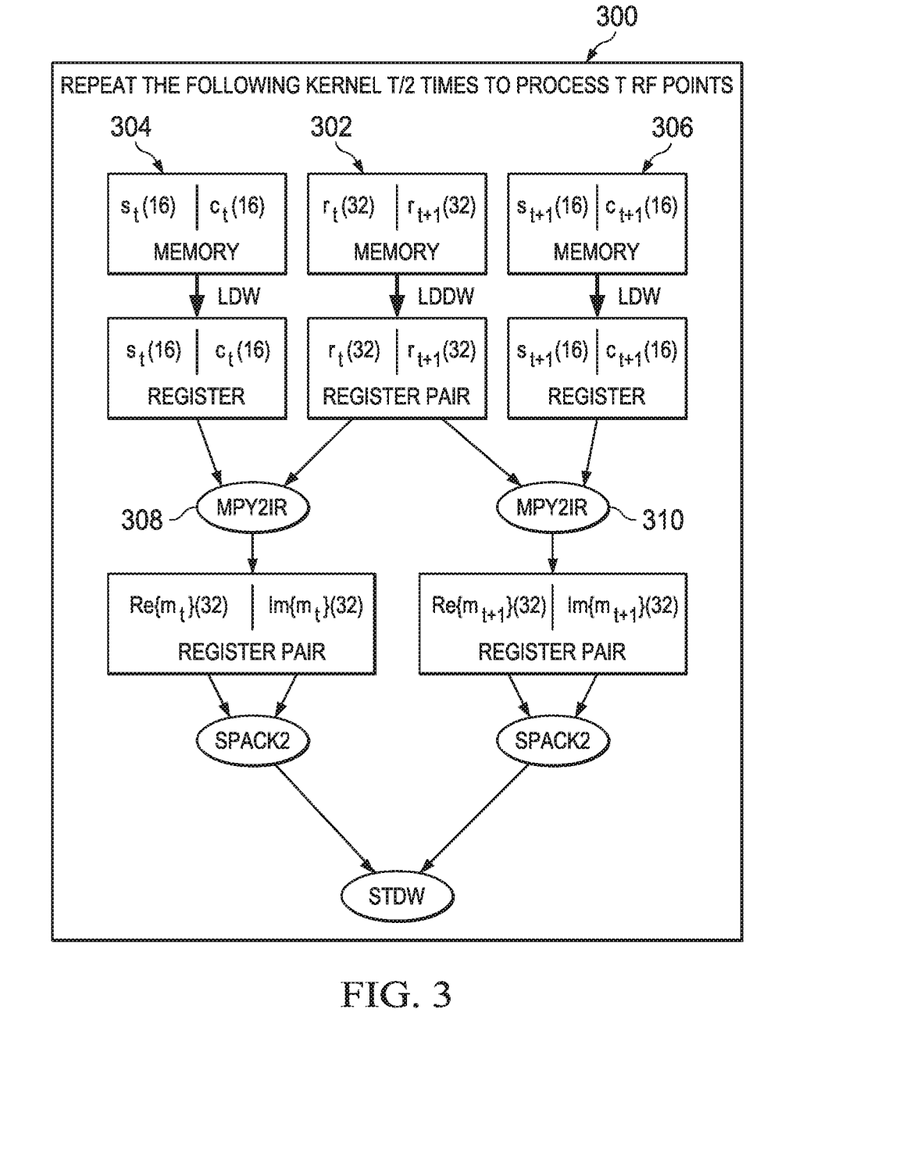
FIG. 3 shows a processing flow diagram for performing radio frequency demodulation mixing in a color Doppler imaging system using a VLIW processor in accordance with various embodiments.

FIG. 3 shows a processing flow diagram 300 for performing mixing in a color Doppler imaging system using a VLIW processor in accordance with various embodiments. For the sake of simplicity, table indexing has been omitted from FIG. 3. In block 302, RF values $r_t$ and $r_{t+1}$ are read from memory and loaded into registers. In blocks 304 and 306, sine and cosine values corresponding to the RF values are read from memory and loaded into registers. In blocks 308 and 310, the RF values are multiplied by the sine and cosine values. The results are stored in registers. The 32-bit register outputs are saturated to 16-bit values, and the four 16-bit values are stored in memory.

Mapping the operations/instructions of FIG. 3 to the functional units of FIG. 2 produces the results shown in Table 1. Adding up the cycle-usage on the four types of processing units (L 210A/B, D 216A/B, S 212A/B, M 214A/B), shows that the D units 216A/B would take the most cycles for this algorithm, despite using the most efficient instructions available. Hence, this kernel can be considered to be "load-limited" and would need approximately T cycles for processing T RF points, achieving a (best-case) performance of one pipelined kernel cycle per output point. Note that by virtue of the data flow chosen, and consequent use of intrinsics, the S units 212A/B also need of one pipelined kernel cycle per output point.

TABLE 1

Mixing Operation Complexity Analysis

| Operation | Cycles | C64x+ ™ Instruction | CPU Unit |
|---|---|---|---|
| Loads - Input | T/4 | LDDW | D1/D2 |
| Loads - Sine/Cosine | T/2 | LDW | D1/D2 |
| Multiplies | T/2 | MPY2IR | M1/M2 |
| Adds (Table indexing) | T/4 | ADD | L1/L2/S1/S2 |
| Saturate/Pack | T/2 | SPACK2 | S1/S2 |
| Modulus (Table indexing) | T/2 | EXTU | S1/S2 |
| Stores | T/4 | STDW | D1/D2 |

The mixing kernel described above, is typically followed by the decimation kernel, which applies an anti-aliasing filter in addition to reducing the sampling rate by a factor of S. The decimation operation involves filtering across the T depth points for each scan-line. At least some embodiments, employ a polyphase implementation which is conceptually similar to clocking the mixed input samples into two filters (one for the real and one for the imaginary parts) every cycle of the up-sampled clock, but clocking out a complex output only every $S^{th}$ clock cycle (every clock in the down-sampled domain). The decimation portion of the RF demodulator block takes TRF input samples and outputs D (T/S) decimated samples. Thus, the filter (and its associated adds and multiplies) runs in the down-sampled domain.

Figure 4:
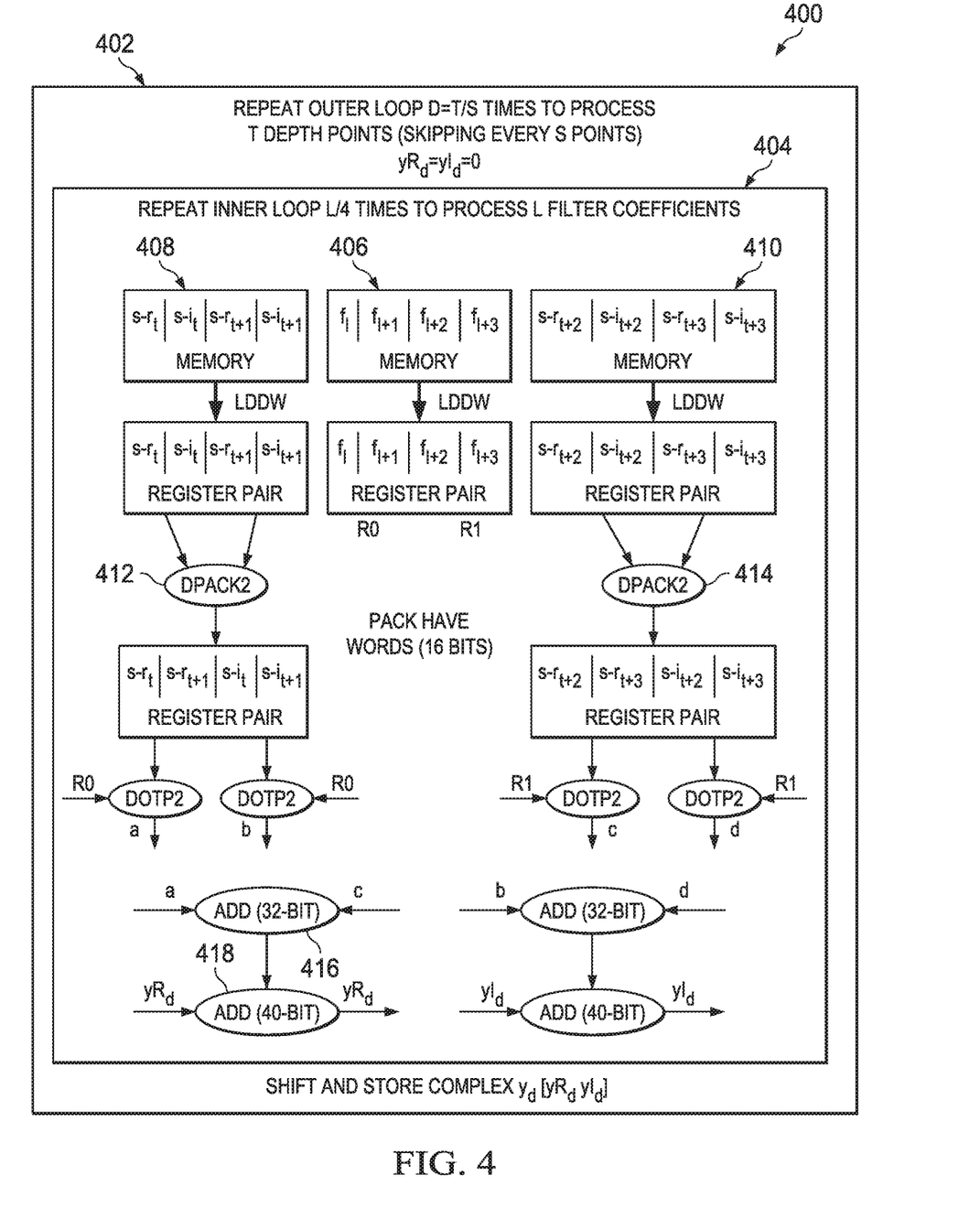
FIG. 4 shows a processing flow diagram for performing radio frequency demodulation decimation in a color Doppler imaging system using a VLIW processor in accordance with various embodiments.

FIG. 4 shows a processing flow diagram 400 for performing RF demodulation decimation in a color Doppler imaging system using a VLIW processor in accordance with various embodiments. The flow comprises an outer loop 402 and an inner loop 404. The outer loop 402 runs only D, rather than T, iterations although the filtering operation may use all T input points. During each of the inner loop 404 iterations, four filter coefficients 406 are read from memory and consumed. Similarly, four complex RF values are read from memory (408, 410) and repacked (412, 414). The repacked data is processed via dot product and summation. Note the use of the intermediate 32-bit add (416) and the final 40-bit add (418). This distinction is notable because 32-bit adds can be performed on L 210A/B, S 212 A/B and D 216A/B units whereas 40-bit adds can take place only on L units 210A/B. Hence 32-bit adds should be used wherever possible. In addition, minimizing use of the L units 210A/B, allows the L units 210A/B to be used for efficient packing instructions like DPACK2 412, a parallel implementation of PACK2 and PACKH2 operations (packs lower 16-bits of two words and upper 16-bits of two words), which only runs on the L units 210A/B.

Table 2 shows a mapping of the operations/instructions of FIG. 4 onto the functional units of FIG. 2. The mapping shows that the decimation operation would be multiplier-limited since the M units 214A/B would need DL/2 cycles to complete their operations while the D 216A/B and S 212A/B units would need fewer cycles to complete their operations. Again, by virtue of the data flow chosen, and therefore the usage of intrinsics, the L units 210A/B also need of DL/2 cycles to complete their operations. Note that the above analysis ignores the overhead for loop counter updates, pointer increments and filter circular indexing, but that such operations can be accommodated them on the unused D 216A/B and S 212A/B units.

TABLE 2

Decimation Complexity Analysis

| Operation | Cycles | C64x+ ™ Instruction | CPU Units |
|---|---|---|---|
| Loads - Input | DL/4 | LDDW | D1/D2 |
| Loads - Filter | DL/8 | LDDW | D1/D2 |
| Multiplies | DL/2 | DOTP2 | M1/M2 |
| Data manipulation | DL/4 | DPACK2 | L1/L2 |
| Adds (40-bit) | DL/4 | ADD | L1/L2 |
| Adds (32-bit) | DL/6 | ADD | S1/S2, D1/D2, L1/L2 |

For improved pipelining, another (identical) set of operations may be performed inside the inner loop. To achieve this, embodiments unroll the outer loop (and process two depth points in parallel), instead of further unrolling the inner loop (and processing eight filter coefficients in parallel). This is because every time the inner loop is unrolled, the overhead (epilog/prolog) of the loop increases, and the overhead is executed D times. In contrast, unrolling the outer loop results in increasing its overhead (which is executed just once) and executing the inner loop overhead only D/2 times. Additionally, by unrolling the outer loop, L can be a multiple of four and D can be a multiple of two, rather than L being a multiple of eight. Using these constraints, at least some embodiments achieve pipelined kernel performance of L/2 cycles per output point.

To provide for operation in systems with limited memory, embodiments allow the filter memory to be set and returned, thereby allowing a software embodiment to be called multiple times to process partial sections of the scan-line. This increases the overhead slightly since separate loops are used to process the first L samples at the start and the state vector is updated before exiting the function.

Returning now to the Wall filter 114, the Wall filter 114 is a high-pass filter used to reduce high-amplitude, low-velocity echoes from vessel walls, also called wall thump. Embodiments implement the Wall filter 114 as an infinite impulse response ("IIR") filter because the Wall filter's response should be very sharp. However, since it needs to filter very short sequences (of ensemble size N), the transient performance of the Wall filter 114 is important. To gain greater control over its transient performance, embodiments employ a state-space formulation of the IIR filter. This filter can be used with different types of initialization—the most common forms being step and projection initialization schemes. For additional information on the filter formulation see Steinar Bjaxum et al., *Clutter Filter Design for Ultrasound Color Flow Imaging*, IEEE TRANSACTIONS ON ULTRASONICS, FERROELECTRICS, AND FREQUENCY CONTROL, February 2002, at 204, which is incorporated herein by reference in its entirety.

The basic operation performed for filtering each scan-line set is a multiplication of complex input data matrix, X, with real coefficient matrix, W given by, $$Y_{D \times N} = X_{D \times N} \cdot W_{N \times N}, \quad (3)$$

Both the input and output data matrices include D rows (corresponding to the D depth points) and N columns (corresponding to the N ensembles). Note that the matrix X is created from N decimated scan lines, E, forming the ensemble. The filter coefficient matrix W includes N rows and N columns. Embodiments may pre-compute the matrix W.

Figure 5:
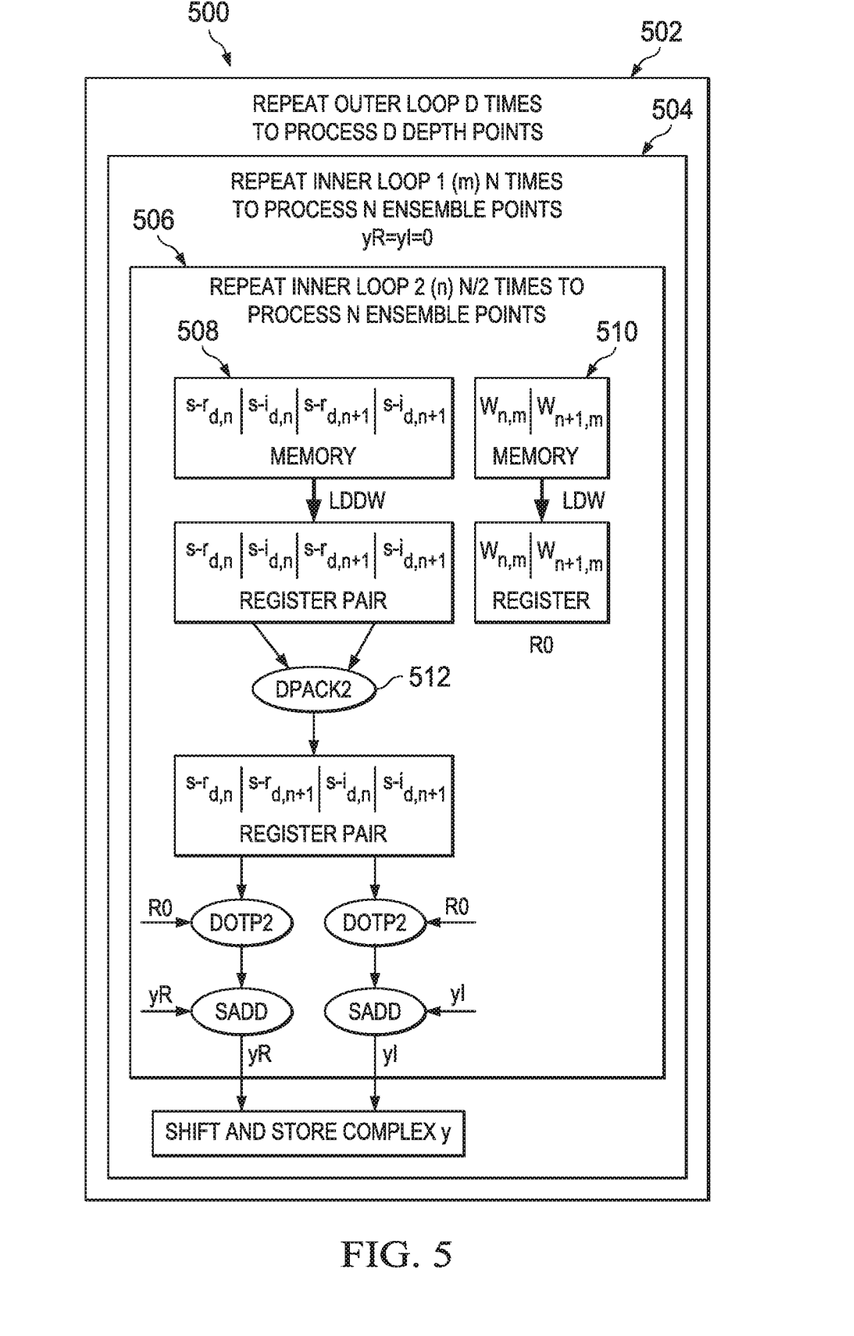
FIG. 5 shows a processing flow diagram for implementing a Wall filter in a color Doppler imaging system using a VLIW processor in accordance with various embodiments.

FIG. 5 shows an exemplary processing flow diagram 500 for implementing a Wall filter in a color Doppler imaging system using a VLIW processor in accordance with various embodiments. The flow includes processing loops 502, 504, and 506. In order to load filter coefficients efficiently, embodiments store the filter coefficient matrix W column-wise in memory (i.e., the transpose of the coefficient matrix W is stored). By storing the transpose of the coefficient matrix, the coefficients on the same column of W, are stored in adjacent memory addresses and can be 64-bit aligned and loaded using wide-load instructions for multiplying the rows of the input matrix. The input and output data are preferably arranged ensemble-by-ensemble, i.e. all the N input/output points at a given depth point, d, lie adjacent to each other in memory, before the N input/output points of the next depth point.

As shown in equation (3) and FIG. 5, the filtering operation comprises multiplication of a complex matrix with a real matrix. Complex samples (508) and filter coefficients (510) are read from memory. The samples are repacked (512) and processed with the filter coefficients and prior filter outputs to produce a complex filtered data sample. Some embodiments can employ multiple such kernels in parallel in order to improve pipelining and to allow use of efficient shifting, packing and storage instructions in the last stage.

Table 3 shows an exemplary mapping of the operations of FIG. 5 to the functional units of FIG. 2. The mapping of Table 3 shows that the M units 214A/B are most heavily used as they are used for the two sets (real and imaginary) of 16×16 multiplies. To generate each of the DN complex output points, 2N real multiplies are needed for each point, taking $DN^2/2$ cycles. Since all other functional units are expected to take fewer cycles than the M unit 214A/B, this embodiment of the algorithm should need $DN^2/2$ cycles for processing D decimated points.

TABLE 3

Wall Filtering Complexity Analysis

| Operation | Cycles | C64x+™ Instruction | CPU Units |
|---|---|---|---|
| Loads - Input | DN/4 | LDDW | D1/D2 |
| Loads - Coefficients | $N^2/2$ | LDDW | D1/D2 |
| Multiplies | $DN^2/2$ | DOTP2 | M1/M2 |
| Adds | $DN^2/4$ | SADD | L1/L2, S1/S2 |
| Data Manipulation | $DN^2/4$ | DPACK2 | L1/L2 |

The pipelined kernel of at least some embodiments achieves performance of N/2 cycles per output point, matching the estimates given above. Note that algorithms involving nested loops need to be implemented carefully because only the innermost loop may be pipelined and the overheads of the inner loops are executed each time the outer loop runs. Typically, the best way to handle such situations is to unroll the innermost loop completely, and thereby reduce the number of loops. If the value of N is known a-priori, this is the preferred approach. However, if it is desired to keep N variable, all three loops 502, 504, 506 should be retained, but each loop may be partially unrolled. Depending on the extent to which each of the loops is unrolled, the cycle-performance of the function may differ, even if the innermost kernel cycles remain the same in each case. This is because of the overheads of the loops change based on the loop unrolling factors. For example, with D=128, N=8 various implementations of the algorithms provided the following cycle complexities:

Theoretical complexity estimate was $DN^2/2$=4096 cycles.

An embodiment retaining all three loops 502, 504, 506 and unrolling each one twice has cycle-performance of 8.9 k cycles. Note that in this embodiment, the real-imaginary bit packing was done inside the innermost loop 506, since there were L/S units available. Only the packing of the final result and storage were done in the level 2 loop 504, thereby reducing the operations that are not pipelined. The embodiment takes $0.5DN^2+3.5DN+9.5D+8$ cycles to process D points. Again, notice that the first term of the equation matched the ideal estimate for the innermost kernel.

By completely unrolling the innermost loop, such that the implementation consists of only two nested loops, an embodiment achieves cycle-performance of 5.7 k cycles.

Turning now to the flow estimators 116, a flow power estimator computes the power of an ensemble of points. Flow power is also estimated by the flow parameter estimator discussed below. A separate implementation is considered here because flow power may be estimated in a variety of contexts. For example, a flow power estimator can be used to calculate the input and output power of the Wall filter 114, to compute a signal-clutter ratio, or be used for detecting the presence of blood in color Doppler processing—when other flow parameters are not used. For a complex input matrix $X_{D \times N} = I_{D \times N} + jQ_{D \times N}$, the output vector $P_D = \{p_d\}$ can be computed as, $$P_d = \sum_{n=0}^{N-1} i_{d,n}^2 + q_{d,n}^2, \quad 0 \le d \le (D-1). \quad (4)$$

Again, the input data may be arranged ensemble-by-ensemble.

Figure 6:
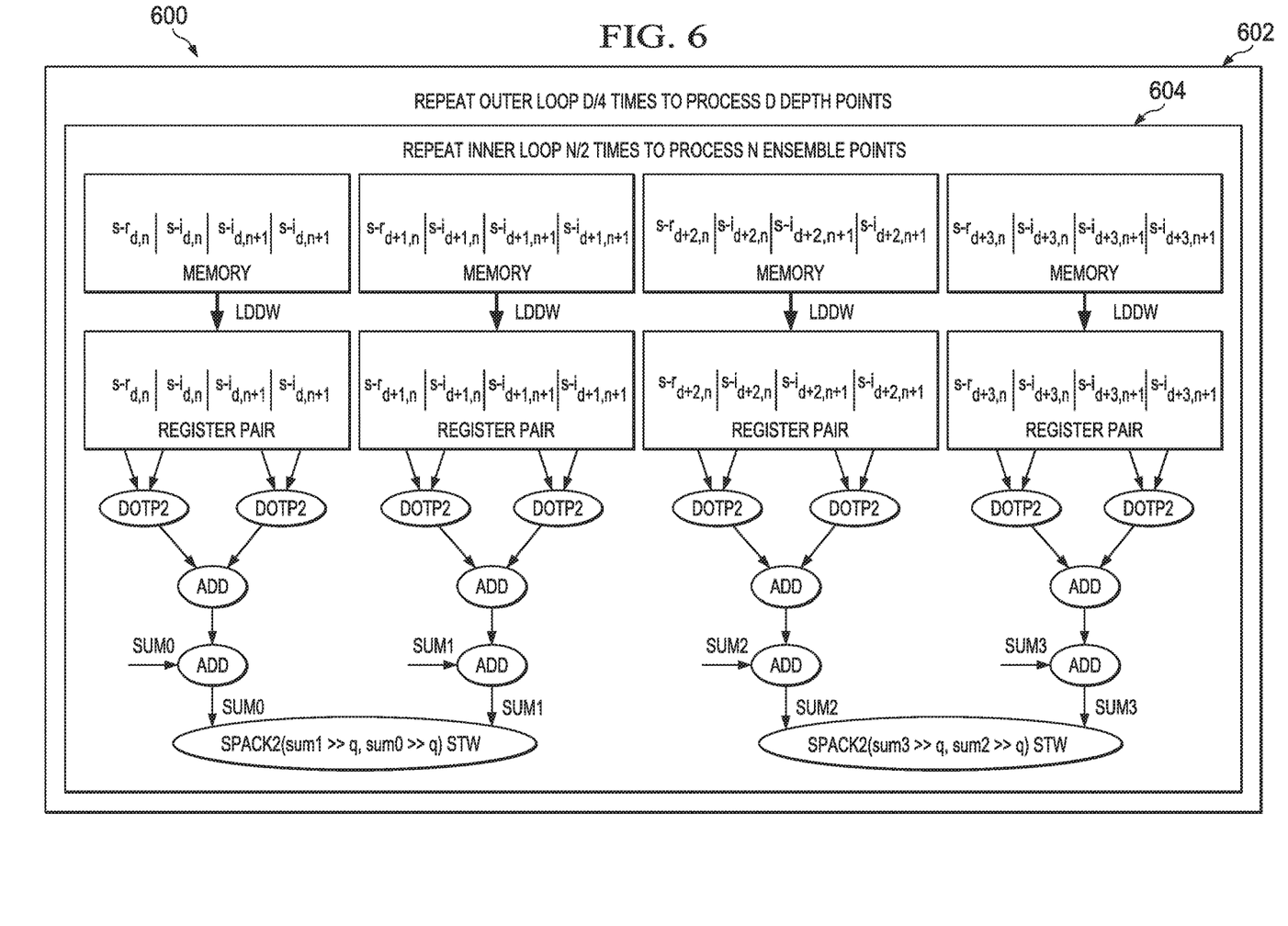
FIG. 6 shows a processing flow diagram for performing flow power estimation in a color Doppler imaging system using a VLIW processor in accordance with various embodiments.

FIG. 6 shows an exemplary processing flow diagram 600 for performing flow power estimation in a color Doppler imaging system using a VLIW processor in accordance with various embodiments. The flow diagram 600 includes an inner loop 604 and an outer loop 602. Both the outer loop and the inner loop have been unrolled in parallel to facilitate scheduling without imposing large multiplicity constraints on N. Another reason embodiments limit the unrolling of the inner loop 604 is to reduce the overhead of the inner loop, which is executed each time the outer loop 602 runs.

Table 4 shows an exemplary mapping of the operations/instructions of FIG. 6 to the functional units of FIG. 2. Table 4 shows that this embodiment is multiply-limited and would need DN/2 cycles to process D decimated points translating to a pipelined performance of N/2 cycles/output point. Note that in this implementation the 40-bit adds (executed on L units 210A/B) take approximately the same number of cycles as the multiplies. However, in some embodiments, some of these 40-bit adds can be replaced by 32-bit adds which can take place on L 210A/B, S 212 A/B, or D 216A/B units. Hence, although both the M 214A/B and the L 210A/B units take the same number of cycles, the cycles taken by the M unit 214A/B are less implementation-dependent and therefore drive the theoretical estimates.

TABLE 4

Flow Power Computation Complexity Analysis

| Operation | Cycles | C64x+ ™ Instruction | CPU Units |
|---|---|---|---|
| Loads | DN/4 | LDDW | D1/D2 |
| Multiplies | DN/2 | DOTP2 | M1/M2 |
| Adds | DN/2 | ADD | L1/L2 |

In at least some embodiments, the inner kernel performance can be matched to the above estimates, i.e. the kernel uses N/2 cycles for each output point. In such an embodiment, all the additions use 40-bit accumulators and the additions are performed by the L units 210A/B. Such an embodiment achieves performance of DN/2+4.5 D+17 cycles for D points.

The flow estimators 116 can also include a flow parameter estimator (i.e., a color flow estimator). The flow parameter estimator uses the output Y of the Wall filter 114 to estimate the blood flow velocity, power and turbulence using autocorrelation based techniques. At depth point d, for computing both velocity, $v_d$, and turbulence, $t_d$, estimates, the flow parameter estimator uses the correlations between adjacent ensemble points, $c_d$, and ensemble power, $p_d$, as shown below, $$p_d = \sum_{n=0}^{N-2} y_{d,n} \cdot y_{d,n}^*, \quad (5a)$$

$$c_d = \sum_{n=0}^{N-2} y_{d,n+1} \cdot y_{d,n}^*, \quad (5b)$$

$$v_d = \tan^{-1}\left\{\frac{\text{Im}(c_d)}{\text{Re}(c_d)}\right\}, \quad (5c)$$

$$t_d = 1 - \text{saturate}\left\{\frac{|c_d|}{p_d}\right\}, \quad (5d)$$

The flow parameter estimator provides flow power, velocity and turbulence estimates. In at least some embodiments, the input, $Y_{D \times N} = y\{d,n\}$ includes packed 16-bit complex values while the power, velocity and turbulence outputs comprise 8-bit real data. For additional information on flow parameter estimation see Chihiro Kasai et al., *Real-Time Two Dimensional Blood Flow Imaging Using an Autocorrelation Technique*, IEEE TRANSACTIONS ON SONICS AND ULTRASONICS, 1985, at 458, which is incorporated herein by reference in its entirety.

Some embodiments of the flow parameter estimator use a DSP math library to implement the four quadrant inverse tangent (_IQNa tan 2), division (_IQNdiv) and magnitude (_IQNmag) calculations. Each of these functions uses 32-bit inputs and produces 32-bit outputs. Lower precision may be sufficient for some embodiments. In at least some embodiments, the correlation outputs are 32-bits and all intermediate sums use 32-bit accumulators.

Figure 7:
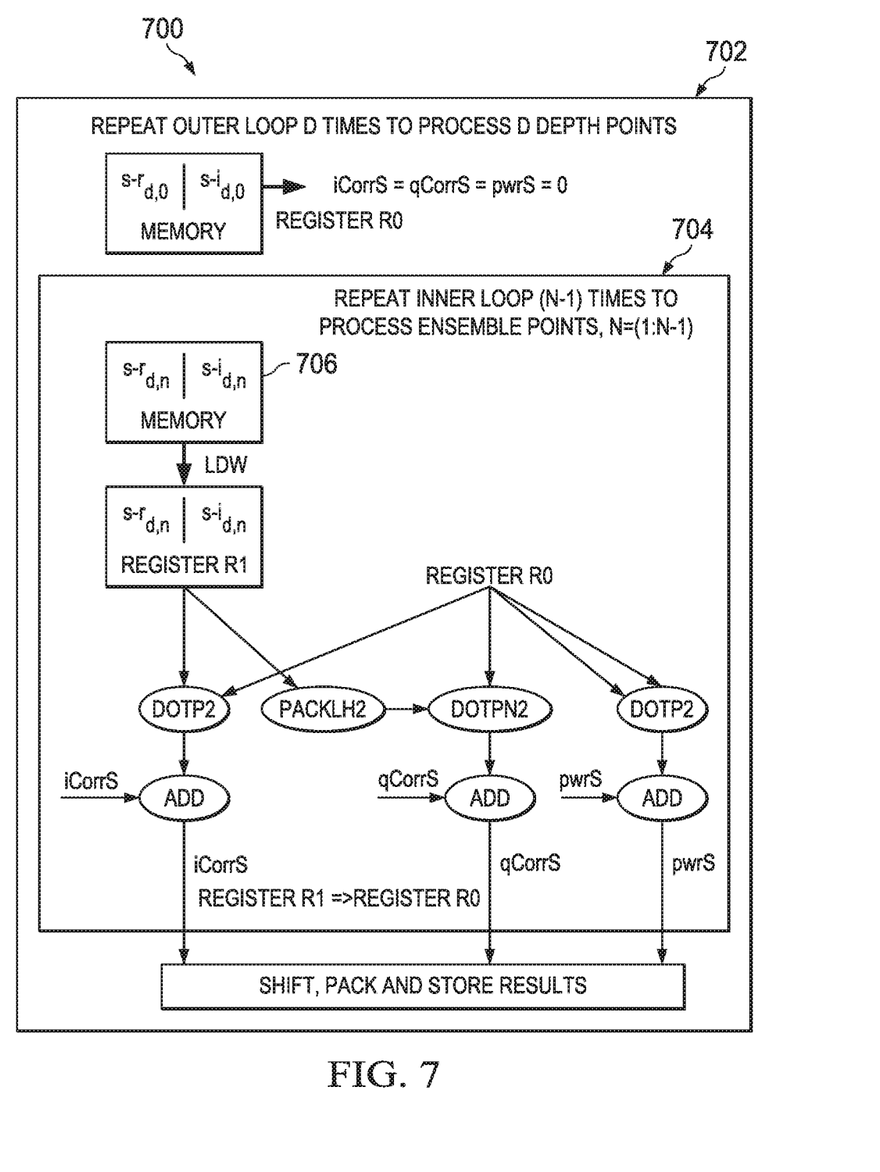
FIG. 7 shows a processing flow diagram for performing correlation and power computations in a color Doppler imaging system using a VLIW processor in accordance with various embodiments.

The flow parameter estimator includes three kernels—one for power and correlation, a second for velocity and a third for turbulence estimates. FIG. 7 shows a processing flow diagram 700 for performing correlation and power computations in a color Doppler imaging system using a VLIW processor in accordance with various embodiments. An inner loop 704 and an outer loop 702 are shown. Packed complex sample values are loaded from memory (706). The complex correlation and real power values are computed using dot product and addition operations. Output values are packed and stored.

Table 5 shows an exemplary mapping of the operations of FIG. 7 to the functional units of FIG. 2, to arrive at an estimate of the complexity of the kernel. Table 5 shows this kernel to be multiply limited, with a minimum of 3DN/2 cycles for processing D decimated points. Per equation (5c), velocity is computed taking the inverse tangent of the correlation at each depth point. In some embodiments, the inverse tangent computation takes ~32 cycles per depth point using a pipelined implementation of _IQNa tan 2. The turbulence calculation involves using _IQNmag and _IQNdiv functions to perform a magnitude and division at each depth point, taking ~13 and ~11 cycles respectively in pipelined implementations. Thus, the turbulence calculation is expected to take ~24 cycles per output depth point, yielding a total pipelined performance of 3DN/2+56D cycles for D points. From this complexity equation, it can be seen that for small values of N, embodiments can achieve significant complexity savings in the velocity and turbulence estimation loops by using lower precision (and complexity) variants of algorithms used for computing magnitudes, divisions and inverses of the tangent.

In at least some embodiments, the outer loop 702 for the correlation-power computation kernel can be unrolled twice in order to achieve optimum performance. Such unrolling of the outer loop 702 allows the functional units to be balanced on each side, minimizes cross paths, and allows the use of efficient packing instructions to pack and store the results for the two depth points at the end of the inner loop 704. Furthermore, some embodiments perform additional operations in the velocity and turbulence computation kernels in order to produce 8-bit results from the 32-bit _IQNa tan 2, and _IQNdiv outputs. Embodiments include an additional saturate operation in the turbulence kernel in order to ensure that the turbulence result always remains positive. Overall, at least some embodiments achieve performance of 3DN/2+62D+234 cycles for D points, with the kernels matching the theoretical projections exactly.

TABLE 5

Correlation and Power Computation Complexity Analysis

| Operation | Cycles | C64x+™ Instruction | CPU Units |
|---|---|---|---|
| Loads | DN/4 | LDDW | D1/D2 |
| Multiplies - correlations | DN | DOTP2, DOTPN2 | M1/M2 |
| - Power | DN/2 | DOTP2 | M1/M2 |
| Adds - correlations | DN | ADD | L1/L2 |
| - Power | DN/2 | ADD | L1/L2 |
| Data manipulation | DN/4 | PACKLH2 | L1/L2, S1/S2 |

At least some embodiments of the flow estimators 116 use two-dimensional computations to produce the flow power, turbulence, and velocity estimates. For additional information regarding flow estimation see Chihito Kasai, referenced supra; Thanasis Loupas et al., *Experimental Evaluation of Velocity and Power Estimation for Ultrasound Blood Flow Imaging, by Means of a Two-Dimensional Autocorrelation Approach*, IEEE TRANSACTIONS ON ULTRASONICS, FERROELECTRICS, AND FREQUENCY CONTROL, July 1995, at 689; Yi Zheng & James F. Greenleaf, *Stable and Unbiased Flow Turbulence Estimation from Pulse Echo Ultrasound*, IEEE TRANSACTIONS ON ULTRASONICS, FERROELECTRICS, AND FREQUENCY CONTROL, September 1999, at 1074 which are incorporated herein by reference in their entirety. Embodiments use echoes at M depth points (adjacent to a depth d) from N scan lines (i.e., MN points) to achieve better performance than embodiments using echo data at only depth d from N scan lines (N points). Embodiments use partial sums to reduce the complexity of the two-dimensional flow estimations.

Given the input complex data, $Y_{D \times N} = \{y_{d,n}\}$ the real flow power outputs, $P_D = \{p_d\}$, are computed as, $$p_d = \sum_{m=0}^{M-1} \sum_{n=0}^{N-1} y_{(d+m,n)} y^*_{(d+m,n)}, \quad (6)$$

The power computation for each input point involves 2 real multiples and 1 add, and since a sum of MN such power estimates are needed for each output point, a baseline (direct) implementation of equation (6) can require about, 2DMN real multiplies for each scan line and D(2MN−1) real adds for each scan line.

Embodiments reduce the computational load by storing a partial sum-of-powers at each depth point in a moving window of size M. Using the partial sum, embodiments obtain each output point by applying 2N multiplications (N for the real part and N for the imaginary part) and 2N+1 additions, as opposed to 2MN multiplications and (2MN−1) additions. Thus for D points, embodiments use 2DN real multiplies for each scan line and D(2N−1) real adds for each scan line, shrinking the overall algorithm to ≈1/M the complexity of the direct implementation with no performance degradation. Additional memory is limited to an extra sliding window buffer to store the M partial sums.

Figure 8:
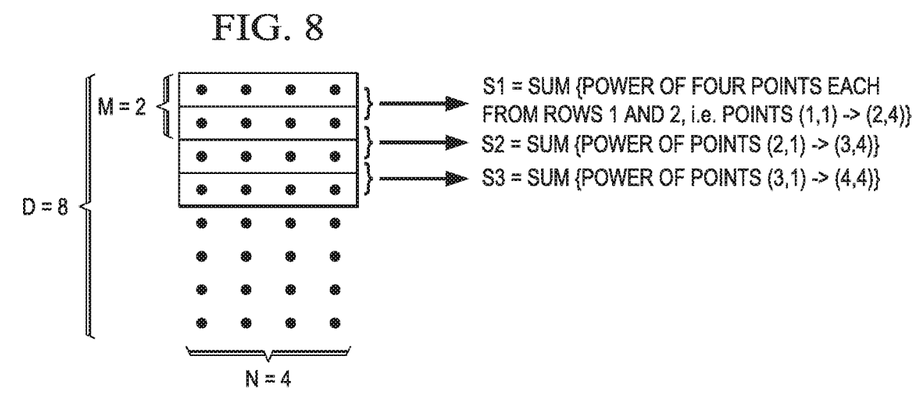
FIG. 8 shows an exemplary application of the direct approach to flow power processing.

FIG. 8 illustrates the direct implementation of equation (6). In FIG. 8, N=4, M=2, and D=8. The direct approach uses 2MN multiplications and (2MN−1) additions at each depth point, resulting in 2DMN multiplications and D(2MN−1) additions for each scan line. As shown in FIG. 8, the sum of powers of points (2, 1) to (2, 4) were used for both S1 and S2 computations. Similarly the sum of powers of points (3, 1) to (3, 4) were used for both S2 and S3 computations and so on.

Figure 9:
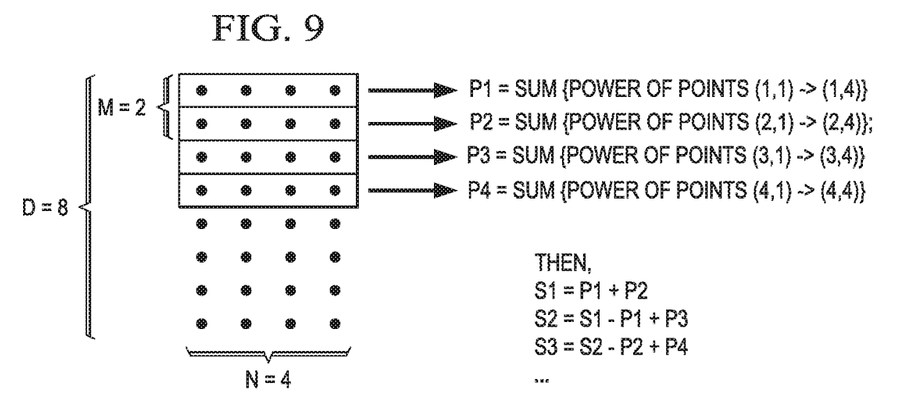
FIG. 9 shows an exemplary application of a partial sums based approach to flow power processing in accordance with various embodiments.

FIG. 9 illustrates the partial sums approach to flow power computation in accordance with various embodiments. A shown in FIG. 9, the sums of powers for each set of N points (P1-P4) are computed, stored, and used to compute multiple flow power values (e.g., P1 is used compute S1 and S2). Thus, the partial-sums approach reduces the number of multiplies to 2N and the number of adds to N+1 for every depth point d.

Embodiments use a similar approach to reduce the complexity of the autocorrelation sums used for velocity and turbulence computations. Both these algorithms compute correlations along the ensemble (corr_n) and depth (corr_m) directions as shown below, $$\text{corr\_n}_d = \sum_{m=0}^{M-1} \sum_{n=0}^{N-2} y_{d+m,n+1} \cdot y^*_{d+m,n}, \quad (7)$$

$$\text{corr\_m}_d = \sum_{m=0}^{M-2} \sum_{n=0}^{N-1} y_{d+m+1,n} \cdot y^*_{d+m,n}. \quad (8)$$

An embodiment using a direct implementation of equations (7) and (8) uses

≈4DM(N−1) real multiplies for each scan line (for ensemble correlation),

≈4D(M−1)N real multiplies for each scan line (for depth correlation),

≈2DM(N−1) real adds for each scan line (for ensemble correlation), and

≈2D(M−1)N real adds for each scan line (for depth correlation).

An embodiment using the more efficient partial sums implementation reduces complexity by a factor of M to ≈4D(N−1) real multiplies for each scan line (for ensemble correlation), ≈4DN real multiplies for each scan line (for depth correlation), ≈2D(N+1) real adds for each scan line (for ensemble correlation), and ≈2D(M+1) real adds for each scan line (for depth correlation).

Table 6 shows exemplary CPU cycles consumed by embodiments of the various modules of the color Doppler imaging system 108 discussed above. As shown, RF demodulation takes the bulk of the cycles. Together all the modules take ~250 MHz of processing power, or ~25% of a 1 GHz DSP. Table 6 also shows that the innermost kernels take most of the cycles in cases of 1-level loops or simple 2-level loops where the inner loop epilog/prolog is small and minimal operations are done in the outer loop, e.g., the flow parameter estimator. In complicated 2 or 3-level nested loops as in the decimation and wall filter kernels, the function takes significantly more cycles than those taken by the innermost kernels.

TABLE 6

Overall complexity of color flow algorithms

| Parameters | |
|---|---|
| | Frame Rate, F, = 30 frames/second |
| | Number of scan line (sets), B,: 64 |
| | Decimation factor, S,: 8 |
| | Number of decimated depth points, D,: 128 |
| | Number of ensembles, N,: 16 |
| | Filter taps, L, = 32 |

TABLE 6-continued

Overall complexity of color flow algorithms

| Module | Innermost kernel cycles (MHz) | Total Cycles (MHz) |
|---|---|---|
| RF demodulation | 94 | 190 |
| Wall Filter | 32 | 48 |
| Flow Parameter Estimation | 20 | 22 |
| Total | 146 | 260 |

The above discussion is meant to be illustrative of the principles and various embodiments of the present invention. Numerous variations and modifications will become apparent to those skilled in the art once the above disclosure is fully appreciated. It is intended that the following claims be interpreted to embrace all such variations and modifications.

What is claimed is:

1. A method of color Doppler ultrasound imaging, comprising:
    receiving radio frequency signals from a front end and beamformer circuit;
    storing in a memory radio frequency values corresponding to said radio frequency signals;
    storing in a memory a sine/cosine look-up table having plural entries, each entry having a sine and a cosine;
    transferring values from the memory to selected ones of a plurality of registers, including register pairs, and operating on the values in selected registers, including:
        transferring a first radio frequency value from said memory to a first register of a first register pair and transferring a second radio frequency value from said memory to a second register of said first register pair;
        rounding a first time value t to a data size corresponding to an index value of said sine/cosine look-up table,
        transferring a first sine value from said memory corresponding to said rounded first time value t to N/2 most significant bits of a third register, and transferring a first cosine value corresponding to said first sine value from said memory to N/2 least significant bits of said third register;
        multiplying said first radio frequency value by said first cosine value generating a first in-phase RF part, and storing it in a fourth register of a second register pair, and multiplying said first radio frequency value by said first sine value generating a first quadrature RF part and storing it in a fifth register of said second register pair;
        transferring N/2 most significant bits of said fourth register into N/2 most significant bits of a sixth register and transferring N/2 most significant bits of said fifth register into N/2 least significant bits of said sixth register;
        rounding a second time value t+1 to a data size corresponding to an index value of said look-up table,
        transferring a second sine value from said memory corresponding to said rounded second time value t+1 to N/2 most significant bits of a seventh register, and transferring a second cosine value corresponding to said first sine value from said memory to N/2 least significant bits of said seventh register;
        multiplying said second radio frequency value by said second cosine value generating a second in-phase RF part, and storing said second in-phase RF part in an eighth register of a third register pair, and multiplying said second radio frequency value by said second sine value generating a second quadrature RF part and storing it in a ninth register of said third register pair;
        transferring N/2 most significant bits of said eighth register into N/2 most significant bits of a tenth register, and transferring N/2 most significant bits of said ninth register into N/2 least significant bits of said tenth register, and
    storing contents of said sixth register and contents of said tenth register into contiguous memory locations in said memory.

2. The method 1, further comprising the steps of:
    storing filter coefficients in contiguous memory locations;
    transferring a third in-phase RF part to N/2 most significant bits of an eleventh register of a fourth register pair, and transferring a third quadrature RF part to N/2 least significant bits of said eleventh register;
    transferring a fourth in-phase RF part to N/2 most significant bits of a twelfth register of said fourth register pair, and transferring a fourth quadrature RF part to N/2 least significant bits of said twelfth register;
    transferring said third in-phase RF part to N/2 most significant bits of a thirteenth register of a fifth register pair, and transferring said fourth in-phase RF part to N/2 least significant bits of said thirteenth register;
    transferring said third quadrature RF part to N/2 most significant bits of a fourteenth register of said fifth register pair, and transferring said fourth quadrature RF part to N/2 least significant bits of said fourteenth register;
    transferring a first filter coefficient to N/2 most significant bits of a fifteenth register of a sixth register pair of the plurality of registers, and transferring a second filter coefficient to N/2 least significant bits of said fifteenth register, and transferring a third filter coefficient to N/2 most significant bits of a sixteenth register of said sixth register pair, and transferring a fourth filter coefficient to N/2 least significant bits of said sixteenth register;
    adding a first product of said third in-phase RF part and the first filter coefficient to a second product of said fourth in-phase RF part and the second filter coefficient forming a first intermediate value a;
    adding a third product of said third quadrature RF part and the first filter coefficient to a fourth product of said fourth quadrature RF part and the second filter coefficient forming a second intermediate value b;
    transferring a fifth in-phase RF part to N/2 most significant bits of a seventeenth register of a seventh register pair, transferring a fifth quadrature RF part to N/2 least significant bits of said seventeenth register;
    transferring a sixth in-phase RF part to N/2 most significant bits of an eighteenth register of an eighth register pair, and transferring a sixth quadrature RF part to N/2 least significant bits of said eighteenth register;
    transferring said fifth in-phase RF part to N/2 most significant bits of a nineteenth register of an eighth register pair, transferring said fifth in-phase RF part to N/2 least significant bits of said nineteenth register, transferring said sixth quadrature RF part to N/2 most significant bits of a twentieth register of said eighth register pair and transferring said sixth quadrature RF part to N/2 least significant bits of said twentieth register;
    adding a fifth product of said fifth in-phase RF part and the third filter coefficient to a sixth product of said sixth in-phase RF part and the fourth filter coefficient forming a third intermediate value c;

adding a seventh product of said fifth quadrature RF part and the third coefficient to an eighth product of said sixth quadrature RF part and the fourth filter coefficient forming a fourth intermediate value d;

adding said first intermediate value a and said third intermediate value c forming a filtered, downsampled in-phase RF part, and adding said second intermediate value b and said fourth intermediate value de forming a filtered, downsampled quadrature RF part.

\* \* \* \* \*